United States Patent [19]

Brakey

[11] Patent Number: 5,893,864
[45] Date of Patent: Apr. 13, 1999

[54] BLOOD LETTING DEVICE

[76] Inventor: Dale Robert Brakey, 92 Belford Road, Kew, Victoria 3102, Australia

[21] Appl. No.: 08/759,258

[22] Filed: Dec. 2, 1996

[30] Foreign Application Priority Data

Dec. 1, 1995 [AU] Australia .................... PN6896

[51] Int. Cl.$^6$ ........................................ A61B 17/32
[52] U.S. Cl. ................... 606/181; 606/167; 606/182
[58] Field of Search ........................ 606/163, 170, 606/172, 181, 182

[56] References Cited

U.S. PATENT DOCUMENTS

| | | |
|---|---|---|
| 3,989,045 | 11/1976 | Van Eck . |
| 4,539,988 | 9/1985 | Shirley et al. ............... 606/182 |
| 4,637,403 | 1/1987 | Garcia et al. ............... 606/182 |
| 4,983,178 | 1/1991 | Schnell . |
| 5,269,800 | 12/1993 | Davis, Jr. . |
| 5,487,748 | 1/1996 | Marshall et al. ............ 606/181 |
| 5,707,384 | 1/1998 | Kim ............................ 606/181 |

FOREIGN PATENT DOCUMENTS

0458451A1  11/1991  European Pat. Off. .......... A61B 5/14

*Primary Examiner*—Michael Buiz
*Assistant Examiner*—Daphna Shai
*Attorney, Agent, or Firm*—D. Peter Hochberg

[57] ABSTRACT

A blood letting device comprising
- a body,
- a base,
- an aperture in the base,
- a sharp with a pointed end, having a rest position and a cocked position,
- biasing apparatus adapted to rapidly urge said sharp from said cocked position to said rest position,
- locking apparatus adapted to hold said sharp in said cocked position,
- wherein the arrangement is such that release of said locking apparatus causes the sharp in moving to said rest position, to prick skin which has been held in the region of said aperture.

19 Claims, 4 Drawing Sheets

BLOOD LETTING DEVICE

FIELD OF THE INVENTION

This invention relates to a blood letting device.

BACKGROUND TO THE INVENTION

There is a need to take blood samples and this is commonly done by pricking a finger with a sharp point but this may involve substantial pain and/or apprehension in a subject whose blood is to be let such that self-administration or administration may be unpleasant.

Further, there is a considerable problem associated with the disposal of the sharp point.

PRIOR ART

Various devices are knows for letting blood but Applicant considers all of tem to have various disadvantages.

SUMMARY OF THE INVENTION

The present invention provides;
a blood letting device comprising
 a body,
 a base,
 an aperture in the base,
 a sharp with a pointed end, having a rest position and a cocked position,
 biasing means adapted to rapidly urge said sharp from said cocked position to said rest position,
 locking means adapted to hold said sharp in said cocked position,
 wherein the arrangement is such that release of said locking means causes the sharp in moving to said rest position, to prick skin which has been held in the region of said aperture.

PREFERRED ASPECTS OF THE INVENTION

The aperture may include a sleeve fitting within the aperture and preferably extending below the base.

Where the device is intended for use in pricking fingers, it is preferred that the internal diameter of the sleeve fully within the range 0.35 to 0.70 cm, more preferably 0.50 to 0.60 cm.

Preferably the lower end of the sleeve has a recess therein which will cause the skin to bulge up within the sleeve as the skin is pressed towards the sleeve so as to bring the skin into proximity with the sharp.

Preferably the sleeve is arranged to turn from a rest position about a hinge when the device is used.

Thus the tamper indicating means may comprise one or more frangible bridges extending between the sleeve and base, said bridge or bridges breaking when the sleeve is turned about the hinge during use.

Alternatively, the tamper indicating means may comprise a latch which prevents the sleeve returning to the rest position.

The biasing means may comprise a resilient arm extending from the base.

The sharp may be provided with a removable cover which protects the user from accidental sticking during handling and maintains a piercing point forming part of the sharp in sterile condition.

Sterilisation of the sharp which may comprise a pointed metal needle may be achieved by moulding the needle in place in plastics using an injection moulder and at the same time moulding the cover in place as well, whereby the needle is substantially enclosed in plastic and the heat of the injection moulding process serves to sterilse the sharp.

An abutment may be provided in the plastic moulded around the needle to engage with a corresponding abutment mounted on the base to act as the locking means.

Thus the locking means may be constructed in such a way that it may be disengaged by pressing upwardly on the sleeve and downwardly on the base in the region where the abutment is mounted on the base.

One or more secondary abutments may be provided on the plastic moulded around the needle to limit the travel of the needle when the locking means is disengaged and/or to provide a finger grip to facilitate manipulation of the sharp into the cocked position.

Preferably the device is arranged so that the pointed end of the sharp is surrounded by the sleeve when the sharp is in the rest position.

The device preferably comprises an integral plastics injection moulding incorporating a metal needle.

The biasing means may comprise a resilient arm extending from the base, the sharp being housed in a sharp carrier mounted on said resilient arm.

In order to illustrate the present invention, a blood letting device in accordance with this invention will now be described by way of example only with the aid of the accompanying drawings.

INTEGER LIST

Figure 1:
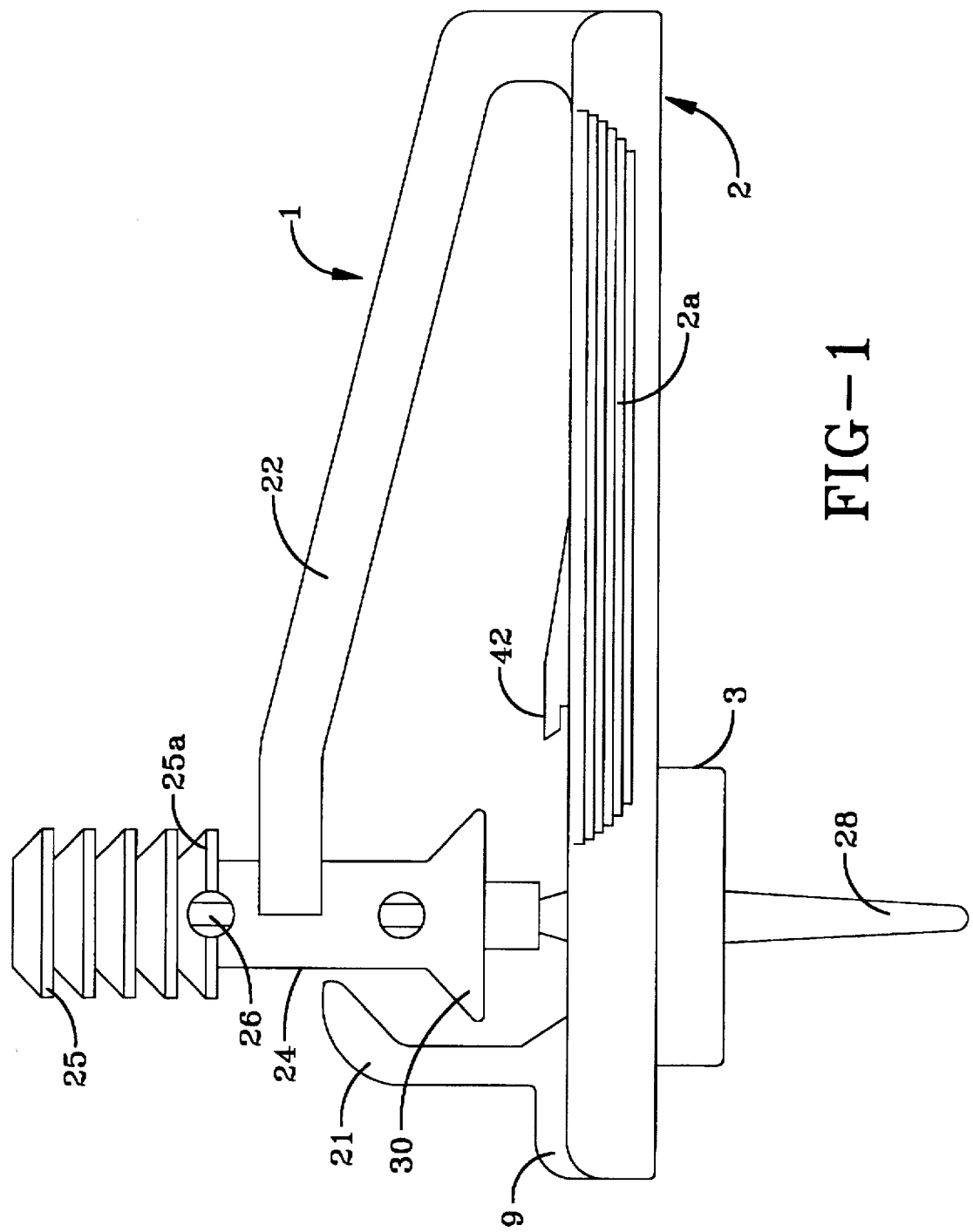
FIG. 1 illustrates an elevational view of a blood letting device constructed in accordance with the invention.

1. Blood letting device
2. Base
2a. Serrations
3. Sleeve
4. Bore
5. Aperture
6. Recess
7. Hinge
9. Arm
21. First abutment
22. Resilient arm
24. Sharp carrier
25. Finger grips
25a. Finger grip
26. Sharp
27. Point
28. Removable cover
29. Break point
30. Second abutment 31. Arrow
42. Latch element
43. Latch element

DETAILED DESCRIPTION WITH RESPECT TO THE DRAWINGS

Figure 2:
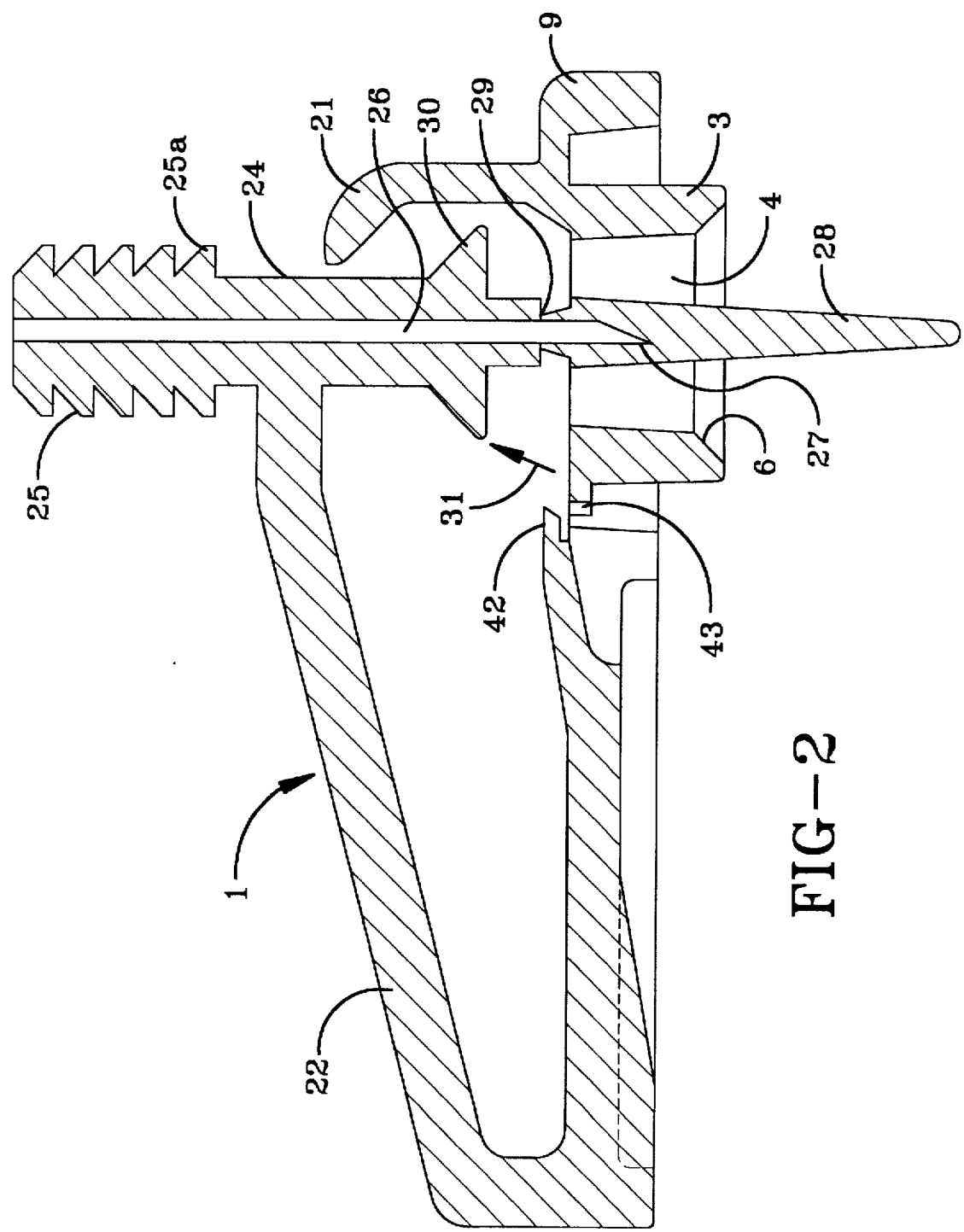
FIG. 2 shows a cross-section of the blood letting device of FIG. 1 which has been rotated through 180° about its vertical axis.
Figure 3:
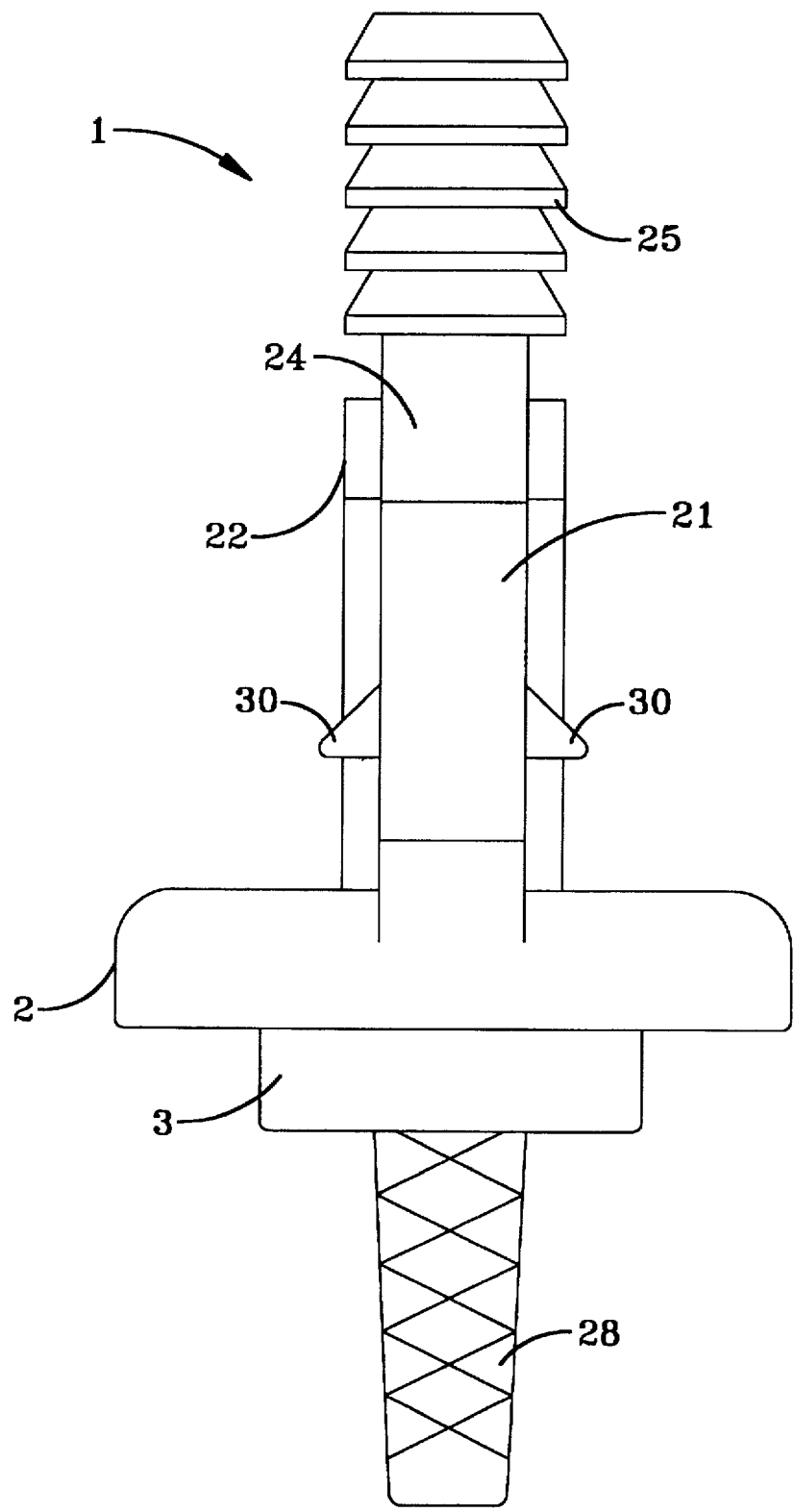
FIG. 3 shows a front on elevational view of the device of FIG. 1.
Figure 4:
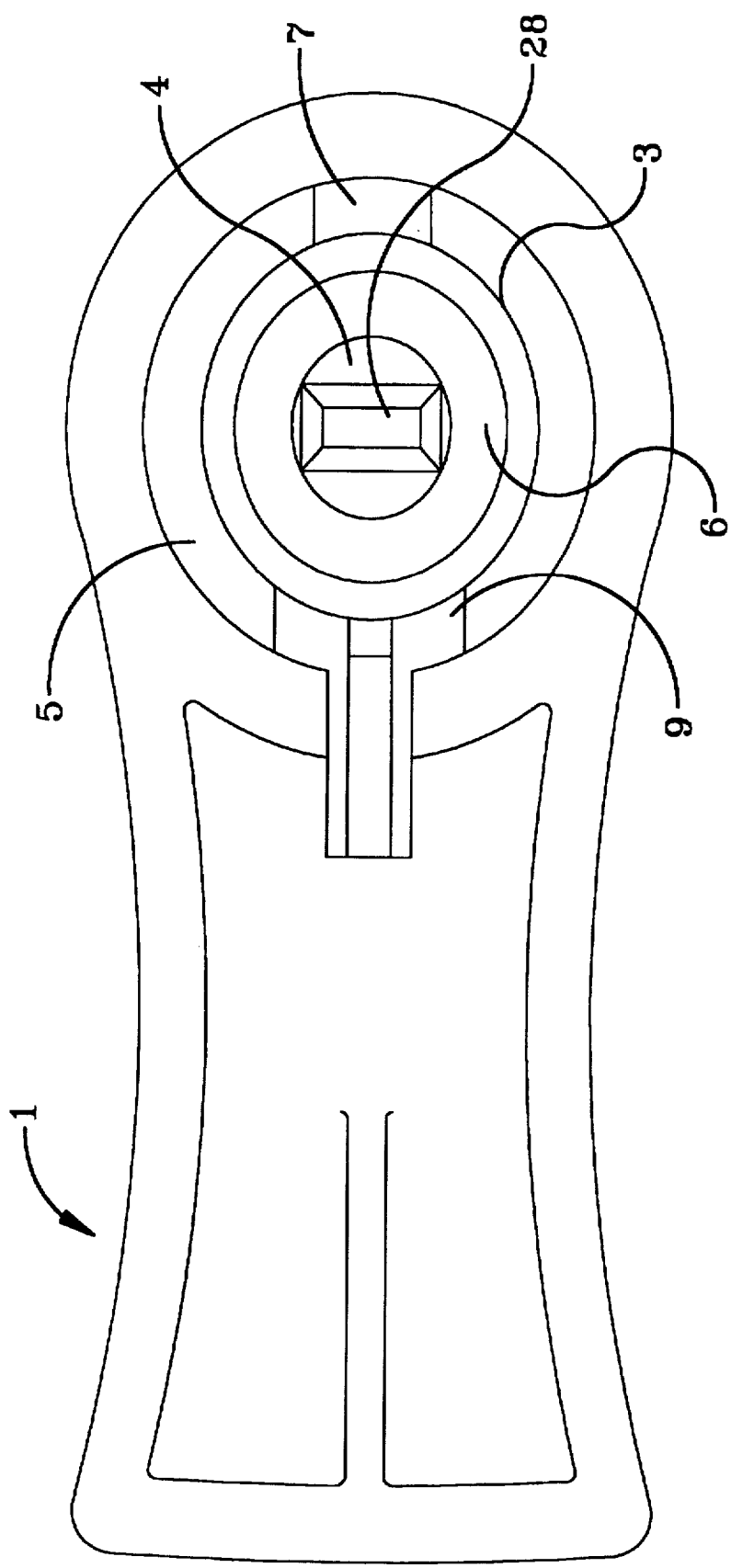
FIG. 4 shows an underside plan view of the device of FIG. 1 rotated about 180° through its vertical axis.

Referring to FIGS. 1-4, the blood letting device generally designated 1 may be formed from any suitable material although it is preferred that the material be a plastic material which is capable of being injection moulded. The injection moulding is preferably as an integral unit with the exception of the needle defining the sharp which may comprise a separate component.

The blood letting device includes a base 2 which may be provided with means to assist gripping such as the serrations 2a.

A sleeve 3 having a bore 4 is located in an aperture 5 formed in the base, the sleeve preferably being provided with an annular recess 6 which may be shaped to assist the blood letting operation.

Thus, the shape of the recess 6 will be such that when a finger or other portion of the anatomy is pushed upwards towards the bore 4, the recess will facilitate bulging of the portion of skin in the bore, thus making it more accessible to being pricked.

A hinge 7 which may simply comprise a bridge joining the sleeve 3 to the base 2. This hinge is preferably integrally formed in the moulding of the plastic forming the blood letting device and, as the preferred plastic will be a resilient material, the hinge will resiliently permit relative movement between the sleeve 3 and the base 2 when pressure is applied to the sleeve by a finger.

An arm 9 is formed at the end of the base 2, and a first abutment 21 mounted on the base in the region of the arm.

A resilient arm 22 extends from and is preferably integral with the base 2 in the manner illustrated.

This resilient arm terminates in the integrally formed sharp carrier 24.

The sharp carrier may be formed with a plurality of finger grip mouldings 25 in the manner illustrated.

The lowermost finger grip 25a may also act as an abutment co-operating with the first abutment 21 to limit downward movement of the sharp carrier during operation.

A sharp 26 which may comprise a metal needle is encased in the sharp carrier 24, the sharp having a point 27 also encased in the removable cover 28 integrally attached to the sharp carrier.

As the sharp is enclosed in plastic by being moulded in situ in an injection moulder, the heat of the plastic used in the injection moulding process should be sufficiently high to sterilise the point of the sharp 27 and thus maintain it in sterilised condition until the removable cover 28 is broken off.

To facilitate removal of the removable cover from the sharp and the sharp carrier, a region of reduced plastic thickness defining a break point 29 may be provided.

The second abutment 30, is arranged to lock the sharp carrier in a cocked position when the sharp carrier is pulled upwards so that the second abutment 30 is higher than and rests on the first abutment 21.

The base 2 and the sleeve 3 are respectively provided with latch elements 42 and 43, the latch elements being shaped to interact in such a way that when the sleeve 3 is pushed upward, the latch element 43 will sit atop the latch element 42 to prevent the sleeve returning to its original position thereby giving a visual indication that the device has been used.

To operate the device, the user twists the removable cover 28 to break it off at the break point 29 and pulls it downwardly off the point 27 of the shaft 26.

Following this the user pulls upwardly on the finger grips 25 to bring the level of abutment 30 above the level of first abutment 21 thereby locking the device in the cocked position.

Upwards finger pressure is then applied to the sleeve whilst at the same time applying downward pressure on the arm 9.

This has the effect of pushing the skin of the finger up into the bore 4 whilst at the same time disengaging the locking action caused by the interaction of the abutments 30 and 21.

Thus the sharp carrier is suddenly released and moves rapidly down to push the point 27 of the sharp through the skin of the user, the lowermost finger grip 25a restricting the extent to which the point 27 may move downwardly.

Having pierced the finger of a user, the point returns to its rest position illustrated in the drawings in the region of the aperture surrounded by the sleeve 3 safely out of harms way should the device accidentally bump against a person during disposal.

At the same time, the sleeve 3 will be locked in a twisted position by the interaction of the latch elements 42 and 43 to indicate that the device has been used.

In addition, the absence of a cover also provides a visual indication that the device has been used.

Other indicator means may also be used to show that the device has been used. These may take the form of a plurality of frangible bridges (not shown) extending between the base around the sides of the aperture 5 to join with the sleeve 3.

The claims, illustrations, photographs and drawings, if any, form part of the disclosure of this specification as does the description, claims, illustrations, photographs and drawings of any associated provisional or parent specification or of any priority document, if any, all of which are imported hereinto as part of the record hereof.

Finally it is to be understood that various alterations, modifications and/or additions may be incorporated into the various constructions and arrangements or parts without departing from the spirit and ambit of the invention.

I claim:

1. A blood letting device comprising:
   a base,
   an aperture in the base,
   a sleeve fitting within the aperture, the sleeve being movable from a rest position,
   a sharp with a pointed end, having a rest position and a cocked position, the sharp being spaced from the sleeve,
   biasing means adapted to rapidly urge said sharp from said cocked position to said rest position,
   locking means operatively connected to the sleeve for releasably holding said sharp in said cocked position, and movable to a release condition in response to movement of the sleeve towards the sharp,
   wherein the arrangement is such that release of said locking means causes the sharp in moving to said rest position, to prick skin which has been held in the region of said aperture, and
   tamper indicating means for indicating when said blood letting device has been used, said tamper indicating means including:

first latching means attached to the sleeve; and second latching means attached to the base;

said first and second latching means cooperating in response to said movement of the sleeve towards the sharp to prevent the sleeve from returning to the rest position, to indicate that said blood letting device has been used.

2. A blood letting device as claimed in claim 1, wherein the sleeve fitting within the aperture extends below the base.

3. A blood letting device as claimed in claim 1, wherein, when the device is intended for use in pricking fingers the internal diameter of the sleeve is within the range of 0.35 to 0.70 cm.

4. A blood letting device as claimed in claim 1, wherein the lower end of the sleeve has a recess therein which will cause the skin to bulge up within the sleeve as the skin is pressed towards the sleeve so as to bring the skin into proximity with the sharp.

5. A blood letting device as claimed in claim 1, and further including a hinge, wherein the sleeve is arranged to turn from the rest position about the hinge when the device is used.

6. A blood letting device as claimed in claim 1, and further including a hinge, the sleeve being turnable about the hinge, and wherein the tamper indicating means comprises at least one frangible bridge extending between the sleeve and the base, said bridge breaking when the sleeve is turned about the hinge during use.

7. A blood letting device as claimed in claim 1, wherein the biasing means comprises a resilient arm extending from the base.

8. A blood letting device as claimed in claim 1, wherein the sharp is provided with a removable cover which protects the user from accidental sticking during handling and maintains a piercing point forming part of the sharp in sterile condition.

9. A blood letting device as claimed in claim 1, wherein the sharp comprises a metal needle, and sterilization of the needle is achieved by moulding the needle in place in plastics using an injection moulder and at the same time moulding the cover in place as well, the needle being substantially enclosed in plastic and the heat of the injection moulding process serves to sterilize the needle.

10. A blood letting device as claimed in claim 1, wherein an abutment is provided in a plastic moulded around the needle to engage with a corresponding abutment mounted on the base to act as the locking means.

11. A blood letting device as claimed in claim 1, wherein locking means may be constructed in such a way that it may be disengaged by pressing upwardly on the sleeve and downwardly on the base in the region where the abutment is mounted on the base.

12. A blood letting device as claimed in claim 1, wherein the sharp comprises a needle moulded in plastic, and the blood letting device further comprising at least one secondary abutment on the plastic moulded around the needle to limit the travel of the needle when the locking means is moved to the release condition.

13. A blood letting device as claimed in claim 1, wherein the device is arranged so that the pointed end of the sharp is surrounded by the sleeve when the sharp is in the rest position.

14. A blood letting device as claimed in claim 1, wherein the device comprises an integral plastics injection moulding incorporating a metal needle.

15. A blood letting device as claimed in claim 1, wherein the biasing means comprises a resilient arm extending from the base, the sharp being housed in a sharp carrier mounted on said resilient arm.

16. A blood letting device as claimed in claim 1 and further including means for impeding re-use of the blood letting device after the device has been used, said means for impeding re-use comprising said first and second latching means cooperating in response to said movement of the sleeve towards the sharp to impede the sharp from returning to the cocked position.

17. A blood letting device according to claim 1, wherein the sharp comprises a needle moulded in plastic, and the blood letting device further comprises at least one secondary abutment on the plastic moulded around the needle to provide a finger grip to facilitate manipulation of the needle into the cocked position.

18. A blood letting device according to claim 1 wherein the sleeve is movable to place the first latching means above the second latching means on the base when the sleeve moves the locking means to the release condition, the first latching means sitting atop the second latching means to prevent the sleeve from returning to its original position.

19. A blood letting device comprising:

a base;

an aperture in the base;

a hinge on the base;

a sleeve movable about the hinge and fitting within the aperture;

a sharp with a pointed end, the sharp having a rest position and a cocked position, the sharp being spaced from the sleeve;

biasing means adapted to rapidly urge said sharp from said cocked position to said rest position;

locking means operatively connected to the sleeve for releasably holding said sharp in the cocked position, and movable to a release condition in response to movement of the sleeve towards the sharp, wherein the sharp moves to the rest position in response to movement of the locking means to the release condition, to prick skin which has been held in the region of the aperture, and tamper indicating means comprising at least one frangible bridge extending between the sleeve and the base, the bridge breaking when the sleeve is moved about the hinge.

* * * * *